(12) United States Patent
Bonnet et al.

(10) Patent No.: US 10,420,941 B2
(45) Date of Patent: Sep. 24, 2019

(54) IMPLANTABLE DEVICE INCLUDING A STIMULATION LEAD FOR BIOIMPEDANCE MEASUREMENT

(71) Applicant: SORIN CRM SAS, Clamart (FR)

(72) Inventors: Jean-Luc Bonnet, Massy (FR); Thierry Legay, Fontenay-lés-Briis (FR); Dominique Decoene, Jouars-Pontchartrain (FR); Patrick Le Gousse, Viry-Châtillon (FR); Mathieu Collignon, Marcoussis (FR)

(73) Assignee: Sorin CRM SAS, Clamart (FR)

( * ) Notice: Subject to any disclaimer, the term of this patent is extended or adjusted under 35 U.S.C. 154(b) by 779 days.

(21) Appl. No.: 14/856,999

(22) Filed: Sep. 17, 2015

(65) Prior Publication Data

US 2016/0082264 A1 Mar. 24, 2016

(30) Foreign Application Priority Data

Sep. 19, 2014 (FR) ...................... 14 58857

(51) Int. Cl.
*A61N 1/36* (2006.01)
*A61B 5/00* (2006.01)
(Continued)

(52) U.S. Cl.
CPC .......... *A61N 1/36139* (2013.01); *A61B 5/021* (2013.01); *A61B 5/0205* (2013.01); *A61B 5/02007* (2013.01); *A61B 5/0535* (2013.01); *A61B 5/0538* (2013.01); *A61B 5/686* (2013.01); *A61B 5/6876* (2013.01); *A61B 5/6877* (2013.01); *A61B 5/7278* (2013.01); *A61N 1/05* (2013.01); *A61N 1/36053* (2013.01); *A61N 1/36114* (2013.01); *A61B 5/024* (2013.01); *A61B 5/026* (2013.01); *A61B 5/02028* (2013.01); *A61B 5/0816* (2013.01)

(58) Field of Classification Search
USPC ............................................. 607/2
See application file for complete search history.

(56) References Cited

U.S. PATENT DOCUMENTS

| 2011/0009754 | A1 | 1/2011 | Wenzel et al. |
| 2014/0121556 | A1 | 5/2014 | Anderson et al. |
| 2015/0289929 | A1* | 10/2015 | Toth ................... A61B 18/1492 600/372 |

FOREIGN PATENT DOCUMENTS

| EP | 1 363 697 | 11/2003 |
| WO | WO-02/18006 | 3/2002 |
| WO | WO-2013/022886 | 2/2013 |

OTHER PUBLICATIONS

Preliminary Search Report for French Patent Application No. 1458857, dated Apr. 28, 2015, 2 pages.

* cited by examiner

*Primary Examiner* — Nicole F Lavert
*Assistant Examiner* — Nicole F Johnson
(74) *Attorney, Agent, or Firm* — Foley & Lardner LLP

(57) ABSTRACT

An implantable device includes a lead, for example for neurostimulation of the vagus nerve. The lead includes a series of stimulation electrodes and a series of external electrodes for bioimpedance measurements on blood flow located in the same region, for example on the carotid artery. The device further includes means for separating into frequency bands the measured bioimpedance signal, the bands selected to reflect different respective activities such as vasomotor activity, hemodynamic activity, respiration, and cardiac rhythm activity.

14 Claims, 7 Drawing Sheets

(51) Int. Cl.
*A61N 1/05* (2006.01)
*A61B 5/02* (2006.01)
*A61B 5/021* (2006.01)
*A61B 5/053* (2006.01)
*A61B 5/0205* (2006.01)
*A61B 5/024* (2006.01)
*A61B 5/026* (2006.01)
*A61B 5/08* (2006.01)

IMPLANTABLE DEVICE INCLUDING A STIMULATION LEAD FOR BIOIMPEDANCE MEASUREMENT

CROSS-REFERENCE TO RELATED PATENT APPLICATIONS

This application claims the benefit of and priority to French Patent Application No. 1458857, filed Sep. 19, 2014, which is incorporated herein by reference in its entirety.

BACKGROUND

The invention relates to "active implantable medical devices" as defined by the Directive 90/385/EEC of 20 Jun. 1990 the Council of the European communities, specifically the devices that continuously monitor heart rhythm and deliver to the heart if necessary stimulation, resynchronization and/or defibrillation pulses of in cases of arrhythmia detected by the device.

The invention relates more precisely to the measurement of hemodynamic parameters.

The measurement of hemodynamic parameters is a key element of the cardiac stimulation. Hemodynamic parameters may include blood pressure measured by a pressure sensor (e.g. strain gauge), cardiac contractility (measured for example by an accelerometer) and heart volumes (measured for example by a conductance sensor in the left ventricle).

These measurements may be used to inform the stimulation device on the effect of a therapy such as cardiac stimulation or neurostimulation at the vagus nerve.

Moreover, in the context of such stimuli, it may be helpful to measure and record information on the patient's physiological condition, such as cardiac and cardiovascular activity, respiratory activity or gastric activity. This allows for application of the stimulation in synchronism with one or more parameters, and for monitoring the effectiveness of the pacing therapy.

For example, for patients with heart failure (typically too low ejection fraction of the left ventricle LVEF in the case of a dilated heart, or a reduction of cardiac volumes with constant LVEF in the case of an enlarged heart), cardiac function can be made more effective by vagus nerve stimulation. In addition, it is known that heart failure is often associated with high blood pressure.

Various solutions have been proposed for measuring hemodynamic parameters related to cardiac activity, in particular to adjust the parameters of a pacemaker.

The known use of a pressure sensor or of an accelerometer in a long-term implanted device may pose many problems, for example durability, the need for a dedicated lead, and power consumption.

As for the systems based on the measurement of the bioimpedance, they require a specific multipolar lead and must be placed in the heart or in the vicinity thereof Another technique is described by WO 2013/022886 A1, consisting of measuring hemodynamic parameters by injecting a current in an organ of a cervical body area and the collection of changes in voltages induced in the vicinity, for example to assess instantaneous changes in the volume of an artery by impedance measurement (impedance plethysmography). In a monopolar configuration, the impedance is measured between the case of the implanted generator and an electrode placed on the vagus nerve, but this configuration does not allow obtaining a measure of the representative local impedance of blood flow in the carotid artery.

In another bipolar embodiment, these local changes can be measured, but any variations in contact impedance of the electrode at the current injection point is likely to cause a variation of voltage, not representative of blood flow. This variation is further capable of creating, in the signal voltage, jumps that may saturate the amplifier stages of the detection circuit of the device.

SUMMARY

The present invention aims to propose a novel bioimpedance sensor capable of performing different types of impedance measurements with a single lead, which can be easily integrated with a sensor dedicated to another function, such as stimulation.

The invention specifically targets the problem of providing signals not affected by any local variations of the contact impedance. The signals accurately reflect changes in the measured hemodynamic parameter, without risk of saturation for the detection circuitry of the device.

This function of a bioimpedance measurement by current injection, with its own problems, must be distinguished from the function of delivering pacing pulses (or of collecting signals produced by an organ), which uses separate electrodes and the configuration of which is specific to the stimulation/detection function. EP 1363697 A2 (published as WO 02/18006 A2) describes a lead for detection/stimulation of the heart chambers, implantable in a coronary vessel. However, in the case of applying voltage pulses or of detecting depolarization potentials (collection of an electrogram), the possible contact impedance variations at the current injection point do not exist.

More specifically, the invention provides an implantable device including, in a manner known per se in particular from WO 2013/022886 A1 cited above, a stimulation lead adapted to be placed into a body region to electrically stimulate. The lead includes a series of pacing electrodes connected to a control device, and a series of electrodes capable of performing bioimpedance measurements on a blood flow in said region.

The series of electrodes include a first pair of electrodes for bioimpedance measurement connected to a current generator for circulating a current in a controlled manner into the blood vessel, and a second pair of electrodes for bioimpedance measurement connected to the input of an amplifying and processing circuit. The second pair of electrodes are configured to detect a signal from which said bioimpedance measurements can be extracted, the signal being generated in response to the current.

Characteristically of the invention, the first and second pair of electrodes for bio-impedance measurement share a common reference electrode.

According to various advantageous subsidiary characteristics:

The electrodes for bioimpedance measurement are arranged flush with the surface of a lead body;

The electrodes for bioimpedance measurement are aligned parallel to an axial direction of the lead;

The amplifying and processing circuit is configured to separate the frequency bands, in particular determining the signal amplitude variations in different frequency bands;

These frequency bands are chosen to reflect at least two activities among vasomotor activity, respiratory activity, hemodynamic activity and a heart rate activity; a frequency band being chosen to determine changes in blood pressure over a cardiac cycle;

The lead is configured to apply neurostimulation to the vagus nerve, and the electrodes for measuring bioimpedance are configured to follow a vessel extending generally in the same direction as the vagus nerve, especially along the carotid artery; the pairs of electrodes for bio-impedance measurement being then separated by a distance about between 10 and 25 mm for a same pair, advantageously with an electrode surface of about 0.5 mm² and 2 mm²;

The device further includes a control circuit capable of controlling the neurostimulation according to the bio-impedance measurements, and then advantageously includes an implantable housing coupled to the lead via a connection including conductors for neurostimulation and conductors for bioimpedance signals from the lead to the housing;

The electrodes of the second pair of electrodes for bioimpedance measurement are configured to detect said signal from which said measurements of bioimpedance can be independently extracted from a contact impedance at the injection point of the current.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the device of the invention will now be described.

Figure 1:
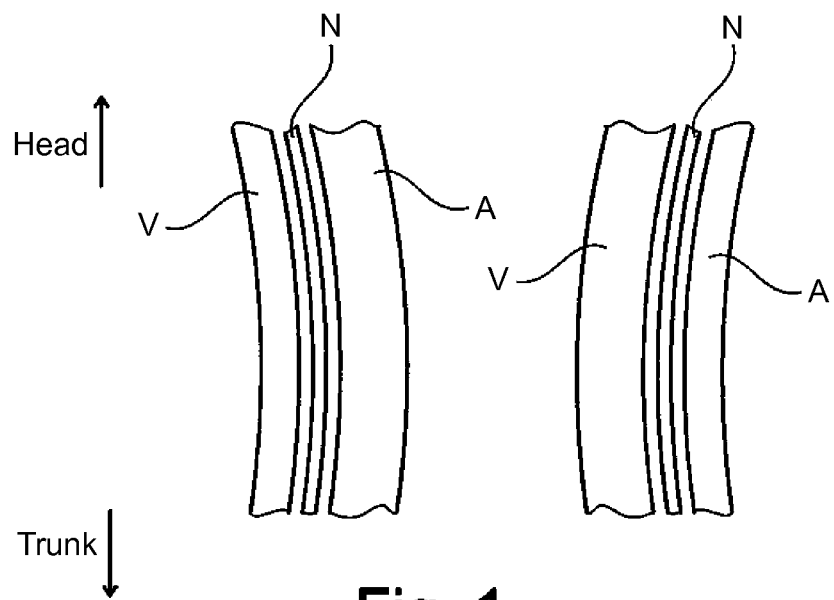
FIG. 1 schematically illustrates the configuration of vagus nerves of the carotid arteries and jugular veins in the neck region of a human being.

Referring first to FIG. 1, both respective left and right systems in the cervical region of the human body (jugular vein V, vagus nerve N, and carotid artery A) are shown.

Figure 2:
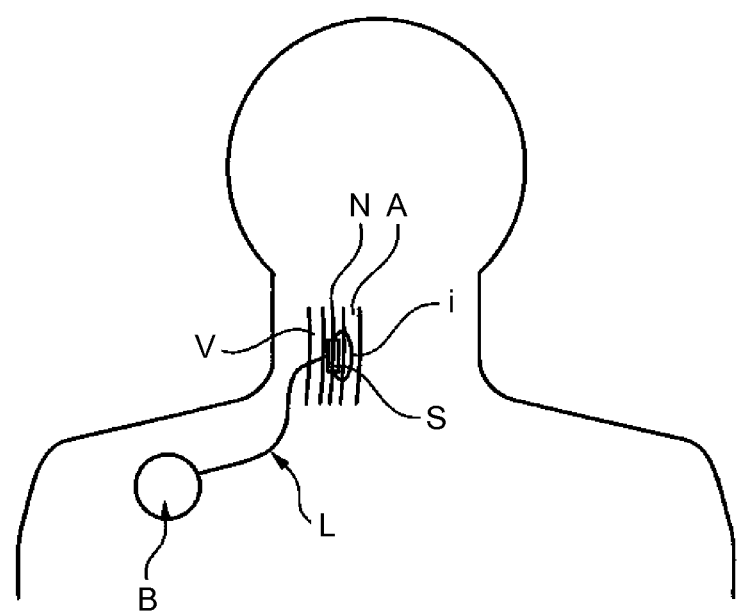
FIG. 2 schematically shows a possible positioning of an implantable device having a lead capable of participating in an impedance measurement.
Figure 3:
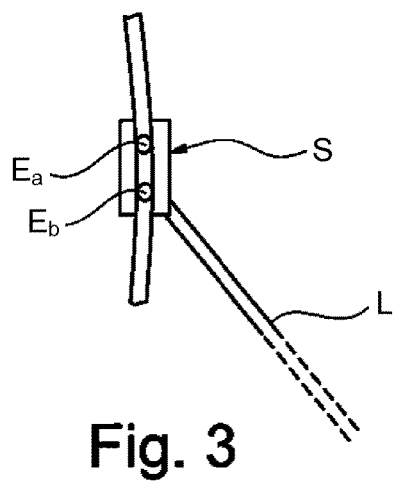
FIG. 3 schematically illustrates a neurostimulation lead placed around the vagus nerve.

Referring to FIG. 2, a lead S for stimulation of the vagus nerve N is implanted and positioned around the vagus nerve, preferably in the cervical region. The lead S is connected to an implantable housing B by a connection L. FIG. 3 schematically illustrates the positioning of the lead S around the vagus nerve. The lead S is equipped with a series of stimulation electrodes, typically a bipolar system including the electrodes $E_a$, $E_b$. In other applications, the system can be quasi-tripolar, tripolar or multipolar, which does not change the principle of the present invention.

The nerve stimulation lead S is also used as an impedance sensor at the carotid artery A, in order to determine variations in impedance in different frequency bands, reflecting the variations of arterial blood flow.

Figure 4:
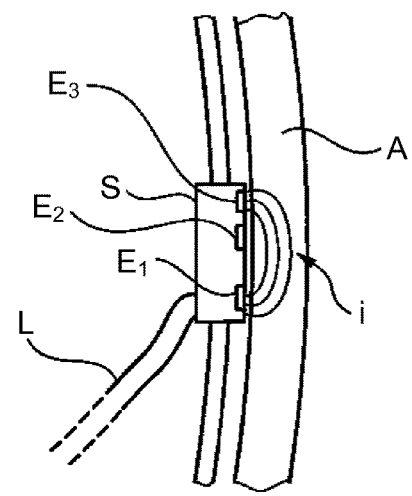
FIG. 4 schematically illustrates the impedance measurement sensing portion of such a lead.

FIG. 4 illustrates in detail the positioning on the vagus nerve of the lead S, which is, according to the invention, a tripolar lead provided with three electrodes $E_1$, $E_2$, $E_3$. The three electrodes $E_1$, $E_2$, $E_3$ are preferably different from electrodes $E_a$ and $E_b$, for the impedance measurement acquisition. There are various current paths i in the artery A between two electrodes $E_1$, $E_3$, whereby a dynamic impedance in the artery will be measured.

Figure 5:
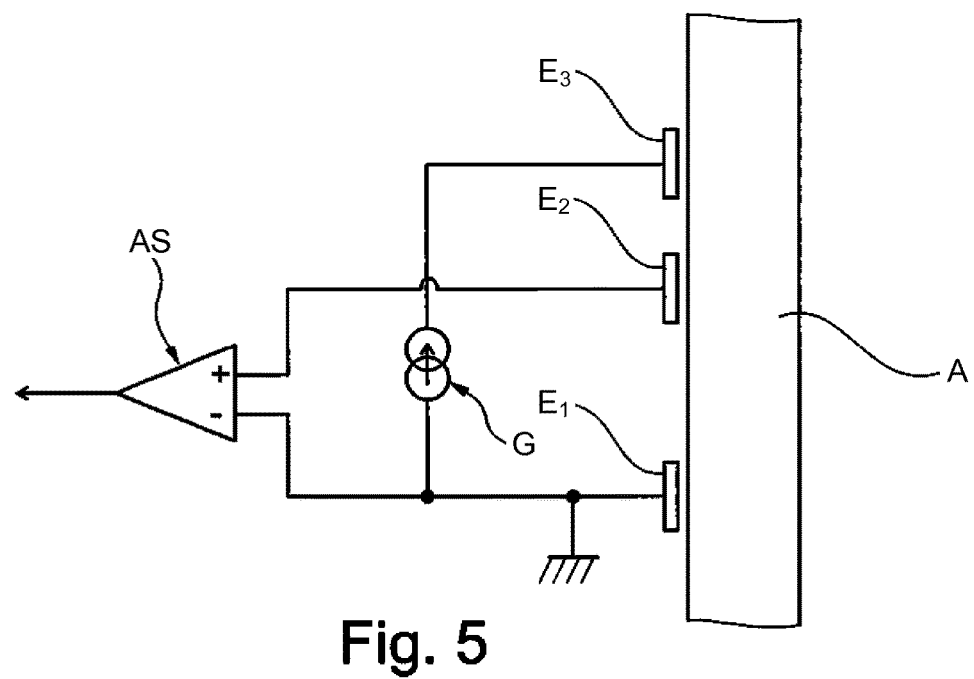
FIG. 5 schematically illustrates a current injection circuit and a current sense circuit for the impedance measurement.

Referring to FIG. 5, the three impedance measurement electrodes $E_1$, $E_2$ and $E_3$ are shown as part of the stimulation lead S and in the vicinity of the blood flow in the carotid artery A, in an alignment generally parallel to the direction of the flow. This electrode assembly includes a reference electrode $E_1$, a current injection electrode $E_3$ and a measurement electrode $E_2$ situated between the two electrodes $E_1$ and $E_3$. The electrodes $E_1$ and $E_3$ are supplied by a current generator G, while the intermediate measurement electrode $E_2$, located closer to the electrode $E_3$ than to the electrode $E_1$, is connected with electrode $E_1$ to the inputs of an output amplifier AS.

Figure 6:
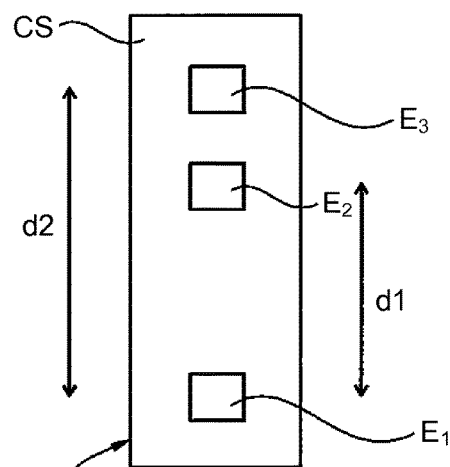
FIG. 6 schematically shows a configuration of electrodes of the lead of FIGS. 3 and 4.

Preferably, and as shown in FIGS. 4 and 6, the electrodes $E_1$, $E_2$, and $E_3$ are made flush in a body CS of the lead S, made of biocompatible insulating material, typically a silicone, so as to face to the carotid artery A.

In one embodiment, the body has a length of about 25 mm. In such an embodiment, the electrodes $E_1$ and $E_3$ may be spaced apart by a distance of about 20 mm, while the distance between the electrodes $E_1$ and $E_2$ is about 15 mm. More generally, the distance between the electrodes $E_2$ and $E_3$ advantageously corresponds to a fraction of the distance between the electrodes $E_1$ and $E_3$ between 5 and 50%, preferably the lowest possible percentage, to maximize the collected electrical field.

The electrodes preferably have an exposed surface between about 0.5 and 2 mm².

Figure 7:
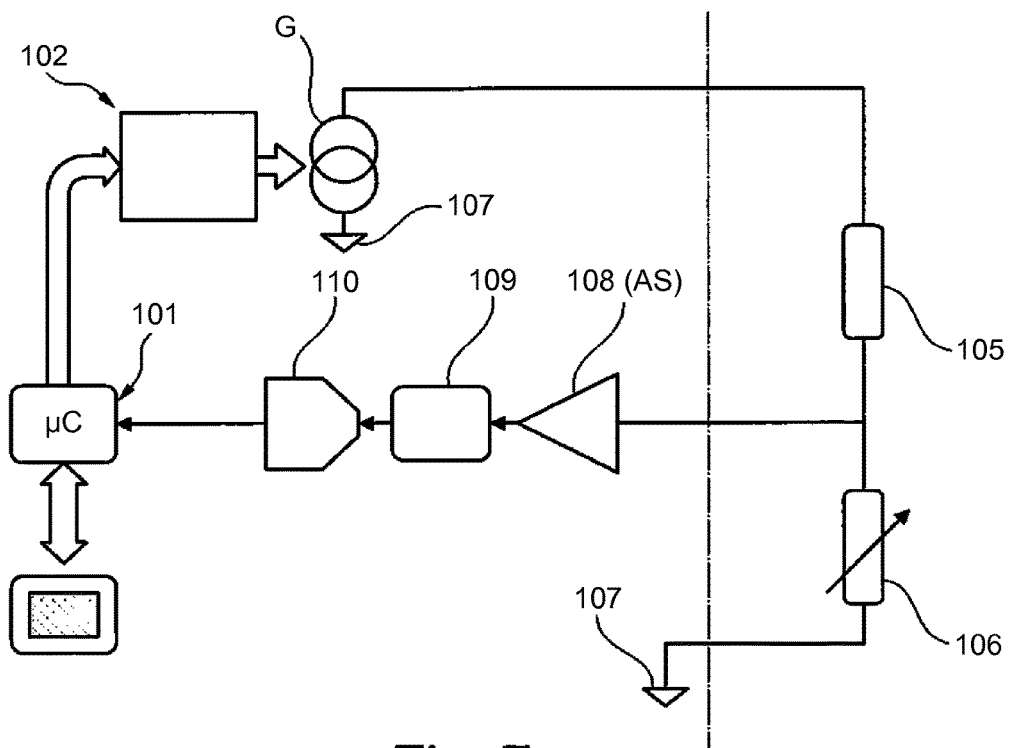
FIG. 7 shows in more detail a current injection and processing circuitry associated with the electrodes.

FIG. 7 illustrates an impedance measurement circuit used with the lead described above.

The circuit includes a microcontroller 101 which drives a current injection control circuit 102. The current injection control circuit 102 acts on the current source G connected to the electrode $E_3$ and to the electrode $E_1$ via the ground 107. A well-defined current is thus injected between the electrodes $E_1$ and $E_3$. This current is preferably pulsed at a frequency between 8 Hz and 128 Hz, the pulses having amplitude between 30 μA and 1000 μA for a width of 5 μs to 50 μs.

The tissues in which this current flows can be approximated to a static bioimpedance, designated by the reference 105 in series with a variable bioimpedance, designated by the reference 106.

The measurement is performed between the electrodes $E_1$ and $E_2$, and the measurement stage includes the voltage amplifier 108 (amplifier AS of FIG. 5) whose output is connected to the input of an analog/digital converter 110 via an analog filter circuit 109. The output of this converter is applied to an input of the microcontroller 101 for processing.

Note that, as a characteristic element of the invention, a third contact point ($E_2$), dedicated to the collection of the signal to be amplified and distinct from the current injection point ($E_3$), is provided.

Therefore, this local tripolar configuration has the advantage, specific to the invention, that the contact impedance present at the current injection point has no effect on the measurement of the signal, and that any changes in the contact impedance does not affect the collection of the voltage to be measured, because of the high input impedance of the amplifier stage AS.

Figure 8:
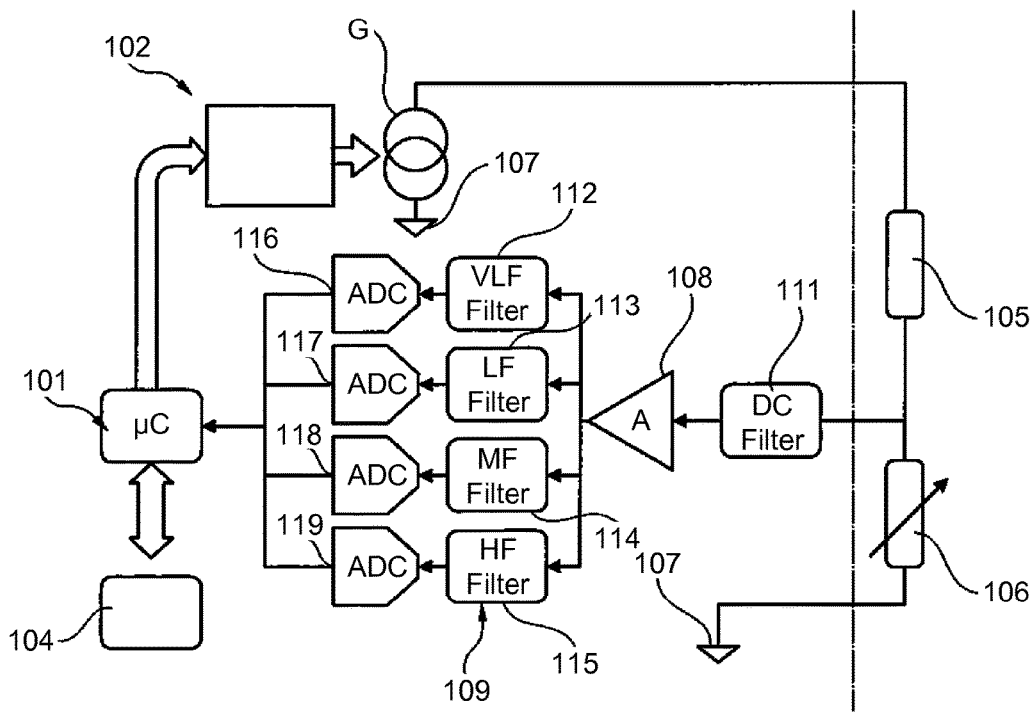
FIG. 8 shows an improved version of the processing circuit of FIG. 7.

In a preferred embodiment, and with reference to FIG. 8, the filtering circuit 109 includes a bandpass filter bank on different frequency ranges, shown as four filters in the embodiment of FIG. 8, for separating the received signal into separate frequency channels. These filters are designated by the references 112 to 115.

The output of each filter is connected to the input of a respective analog/digital converter (references 116 to 119), which can be made by multiplexing the multiple channels into a single converter.

According to an advantageous characteristic, the sampling frequencies of the different converters 116 to 119 are adapted for different frequency bands created by the filters 112 to 115.

As also shown in FIG. 8, a low-cut filter 111 may be provided upstream of the amplifier 108 to remove the DC component of the signal collected at the electrodes $E_1$ and $E_2$.

According to another embodiment, one can apply the output of the amplifier 108 directly to the input of a single analog/digital converter 110, the filtering processing being implemented by digital filtering within the microcontroller 101, or in a dedicated digital signal processor (DSP) 104 associated with the microcontroller.

Figure 9:
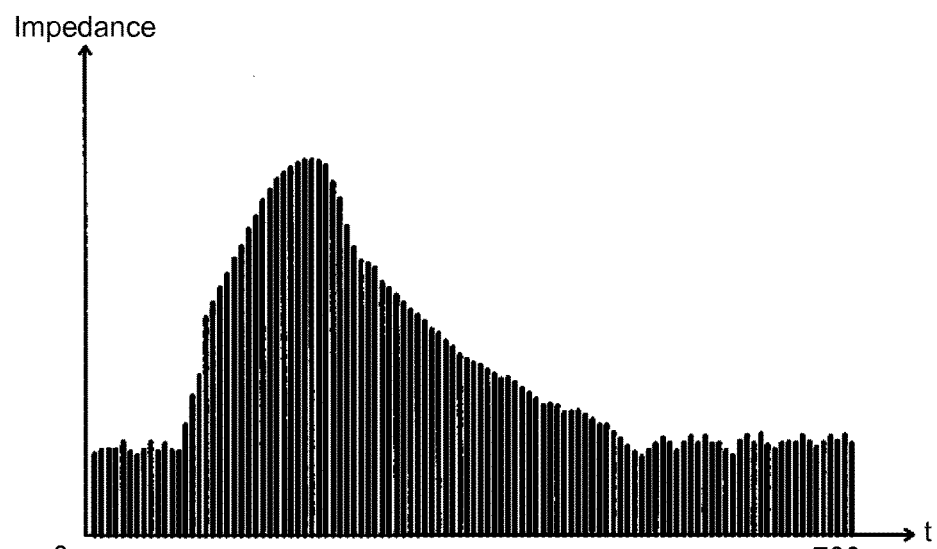
FIG. 9 shows samples of a collected impedance signal.

FIG. 9 illustrates, on a cardiac cycle, the evolution of the raw impedance signal samples collected, on which one can observe that it is representative of the blood pressure.

Figure 10:
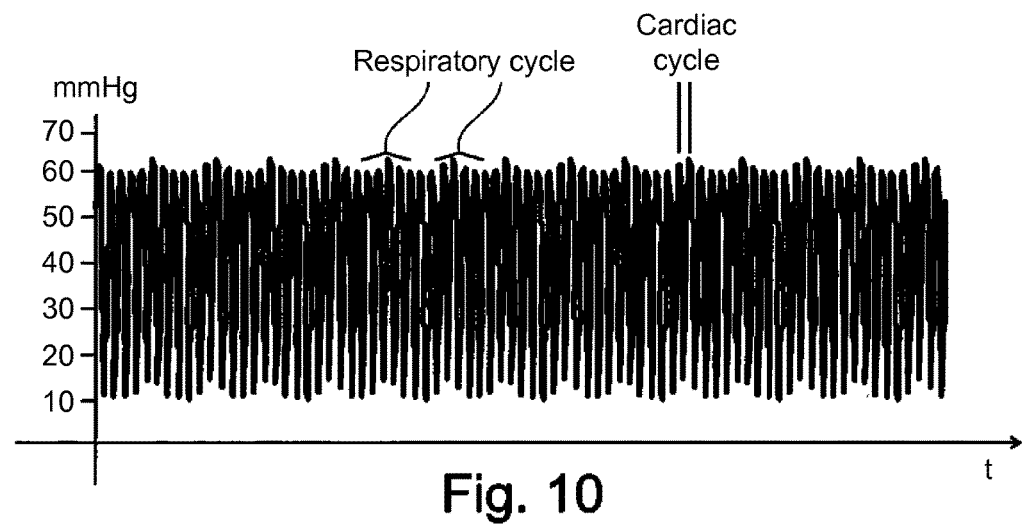
FIG. 10 is an analog representation of a signal collected over a substantially longer period.

FIG. 10 illustrates the extraction, from the collected signal, of a ventricular pressure signal on the cardiac frequency. A modulation of the amplitude of the ventricular pressure signal is detected, which is associated with the respiratory cycle (here an oscillation on six cardiac cycles).

It is therefore understood that by a selective frequency discrimination by filtering as described above, it is possible to discriminatively derive from the signal, changes in various frequency ranges. Typically:

The signal in very low frequencies (typically of the order of 0.1 to 0.2 Hz) contains vasomotor variations, also referred to as Traube-Hering-Mayer waves or THM;

The signal in very low to low frequencies (typically 0.01 to 0.5 Hz) contains variations related to the respiratory function;

The signal in the medium frequencies (typically 1 to 3 Hz) contains variations related to cardiac function; and The signal in the high frequencies (typically up to 50 Hz) contains hemodynamic changes.

Figure 11:
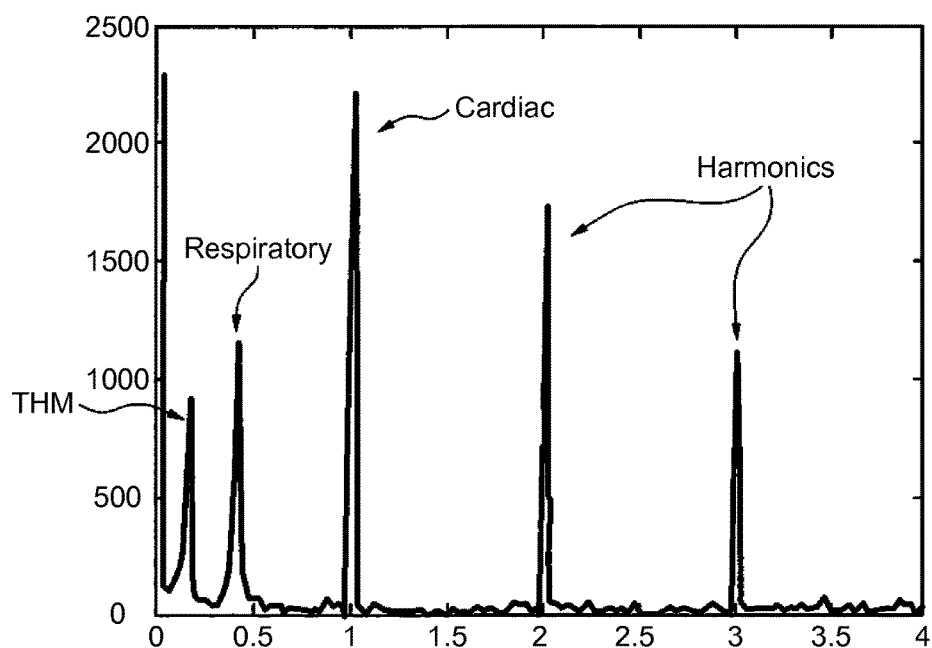
FIG. 11 represents various signal peaks obtained after signal processing.

FIG. 11 illustrates the application of a fast Fourier transform (FFT) on the raw signal to determine its different frequency components. A peak associated with THM waves is observed, a peak related to respiratory function is observed, a peak related to cardiac function is observed, as well as harmonics related to hemodynamic changes in the order of increasing frequencies.

The system can make inferences regarding the effect of a therapy, or to a diagnostic not only by the height and the width of such peaks, but also on the basis of the associated waveforms.

Figure 12:
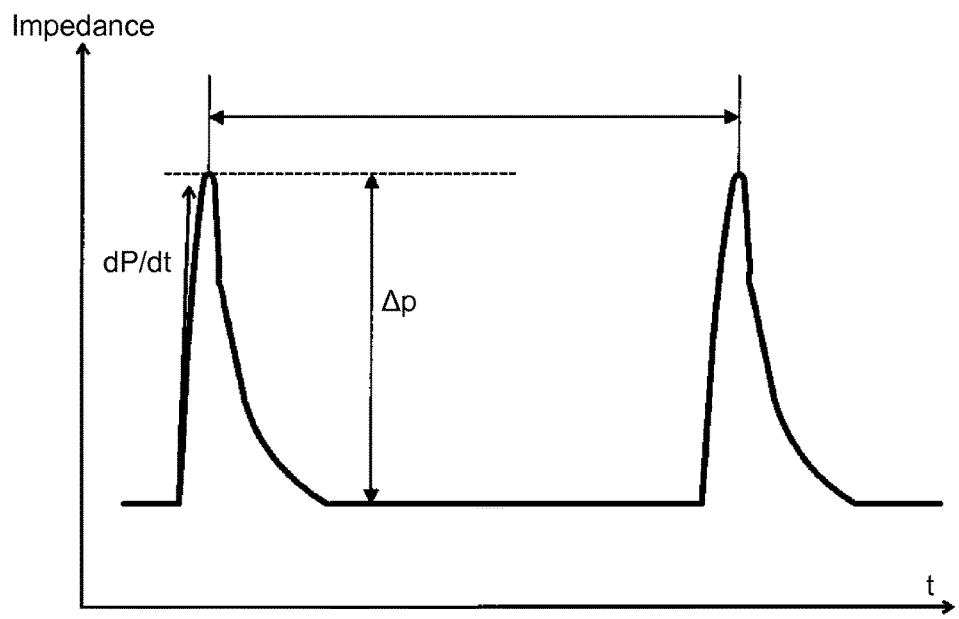
FIG. 12 shows some parameters of a blood pressure signal derived from the collected signal.

Thus, FIG. 12 illustrates the ability to determine among other things the rate of pressure rise during the systolic phase of the ventricle (dP/dt), and the difference between the systolic and diastolic blood pressure ($\Delta P$).

Figure 13:
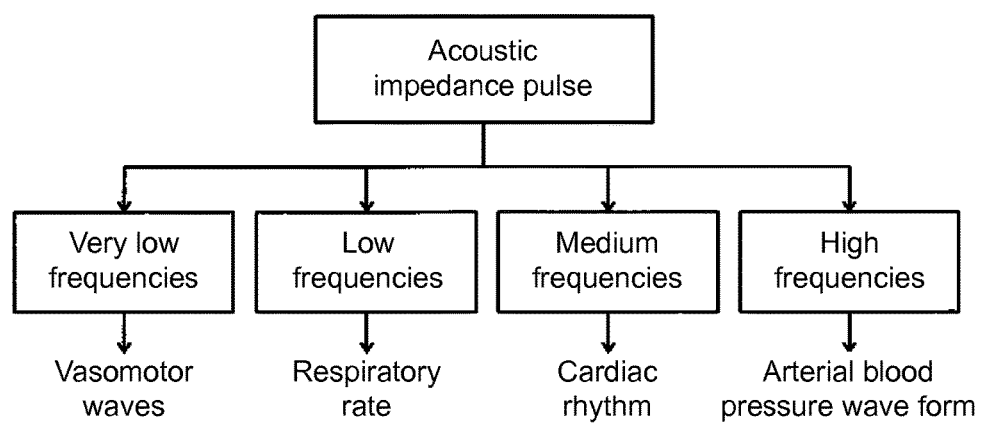
FIG. 13 is a block diagram illustrating the different frequency bands and associated vital functions.

FIG. 13 illustrates in block diagram form the multi-band analysis described in the foregoing disclosure, with some examples of extracted parameters. The invention makes it possible to measure the following parameters, in the frequency bands:

Heartbeat;

Breathing;

Maximum pressure derivative with respect to time during ventricular contraction; and Changes in THM waves over the long term, indicative of changes in vasomotor function.

In one application of the present invention, systolic activity is extracted from the impedance signal to adapt the delivery of neurostimulation therapy. The advantage of this device is to avoid the use of a sensor dedicated to the detection of cardiac activity, such as a lead placed in the right ventricle.

In some embodiments, it is possible to configure an implantable device (e.g. a lead) to enable it to perform bioimpedance measurements on a blood flow in a vessel. In some cases, the implantable device may include a computer storage medium (e.g. a memory) containing instructions which, when executed, implement various process steps in the implantable device.

In other embodiments, the implantable device can allow a current generated by a current source to pass through a first set of electrodes. This current may be simply generated in a controlled manner (i.e., with a value held in a given tolerance range). The implantable device can then measure a signal in response to the current using a second set of electrodes. This signal can then be used to determine the measured bioimpedance. The second set of electrodes may optionally be connected to an input of an amplifying and processing circuit. The first and second set of electrodes can share a common reference. In some embodiments, the signal can further be used to determine one or more parameters such as the heart rate, the respiratory rate, changes in blood pressure, THM wave variations, etc.

Figure 14:
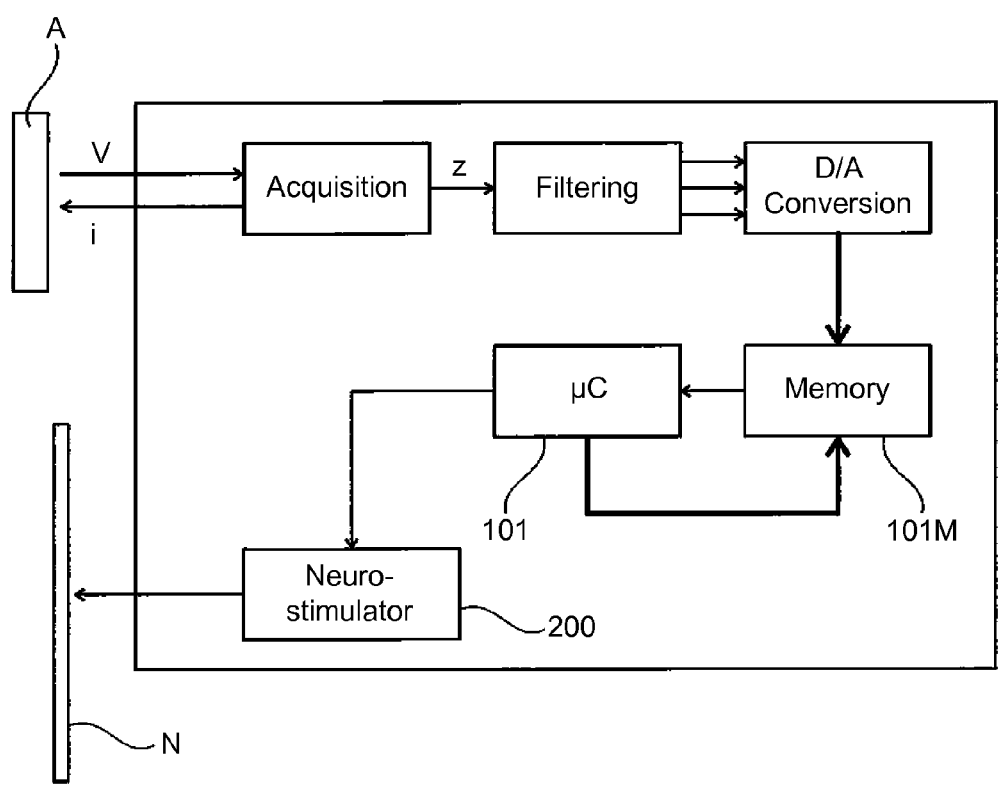
FIG. 14 is a block diagram illustrating the integration of the device for impedance measurement and processing with a neurostimulation lead.

FIG. 14 shows in the form of functional blocks the various components used in a vagus nerve stimulation device equipped with the bioimpedance measurement and analysis device according to the present invention. The data from the analog/digital conversion and the data provided from the frequency analysis described above are stored in a memory 101M associated with the microcontroller 101.

An output of the microcontroller is connected to a control input of a neurostimulation control device 200 located in the implantable housing B. The output is used to apply, to the vagus nerve via the lead S disposed around it, the appropriate cardiac stimulation pulses in response to the analysis of the various parameters from the impedance measurement, performed by the microcontroller with the possible assistance of the digital processor.

Regarding its software aspects, the invention may be implemented by appropriate programming of the controlling software of a known stimulator, for example a cardiac pacemaker, resynchronizer or defibrillator, including the signals delivered from the impedance analysis and optionally from the acquisition methods of a signal provided by endocardial leads.

The invention can thus be applied to any implantable lead located in an environment wherein impedance variations originating from the blood may be observed either in a blood vessel such as the carotid artery, or directly in the heart.

The invention may particularly be applied to implantable devices such as that of Reply and Paradym families produced and marketed by Sorin CRM, Clamart, France.

These devices include programmable microprocessor circuitry to receive, format and process electrical signals collected by implantable electrodes, and deliver stimulation pulses to these electrodes. It is possible to download in it by telemetry software that is stored in memory and executed to implement the functions of the invention that are described below. The adaptation of these devices to the implementation of the functions of the invention is within the skill in the art and will not be described in detail.

It must be noted, to conclude, that the invention is primarily implemented by software, by methods of appropriate algorithms executed by a microcontroller or a digital signal processor. For the sake of clarity, the various processing applied will be broken down and diagrammed by a number of different functional blocks in the form of interconnected circuits, however this representation is only illustrative, these circuits incorporating common elements and in practice corresponding to a plurality of functions performed by a single overall software.

What is claimed is:

1. An implantable medical device, comprising:
   a stimulation lead, comprising:
   a plurality of stimulation electrodes coupled to a control device; and
   a plurality of electrodes adapted to perform bioimpedance measurements on blood flow in a blood vessel, the electrodes including:
      a first pair of electrodes for measuring bioimpedance coupled to a current generator configured to circulate a current in a controlled manner into the blood vessel; and
      a second pair of electrodes for measuring bioimpedance connected to the input of an amplification and processing circuit, and configured to pick up a signal from which the bioimpedance measurement can be extracted, the signal being generated in response to the current;
      wherein the first pair of electrodes for bioimpedance measurement and the second pair of electrodes for bioimpedance measurement share a common electrode forming a reference electrode.

2. The device of claim 1, wherein the first pair of electrodes are arranged flush with the surface of a body of the lead.

3. The device of claim 1, wherein the first pair of electrodes are aligned parallel to an axial direction of the lead.

4. The device of claim 1, wherein the amplification and processing circuit separates the bioimpedance measurement into frequency bands.

5. The device of claim 4, wherein the amplification and processing circuit is adapted to determine the signal amplitude variations in the different frequency bands.

6. The device of claim 5, wherein the frequency bands are chosen to reflect at least two activities among vasomotor activity, respiratory activity, hemodynamic activity and heart rate activity.

7. The device of claim 5, wherein a frequency band is selected to determine changes in blood pressure over a cardiac cycle.

8. The device of claim 1, wherein the lead is configured to apply neurostimulation to the vagus nerve, and wherein the first pair of electrodes for bioimpedance measurement are configured to follow a vessel extending generally in the same direction as the vagus nerve.

9. The device of claim 8, wherein the vessel is the carotid artery, and wherein the first pair of electrodes for bioimpedance measurement are separated by a first distance of greater than about 10 mm but less than about 25 mm and the second pair of electrodes for bioimpedance measurement are separated by a second distance that is less than the first distance.

10. The device of claim 9, wherein the second distance is in the range of 50% to 95% of the first distance.

11. The device of claim 9, wherein the first pair of electrodes of bioimpedance measurement have a surface area between about 0.5 and 2 mm$^2$.

12. The device of claim 9, further comprising a control circuit configured to control the neurostimulation according to the bioimpedance measurements.

13. The device of claim 12, further comprising an implantable housing connected to the lead by a link comprising conductors for neurostimulation and conductors for bioimpedance signal of the lead to the housing.

14. The device of claim 1, wherein the electrodes of the second pair of electrodes are configured to receive the signal from which said bioimpedance measurements can be independently extracted from contact impedance at the injection point of the current.

* * * * *